(12) United States Patent
Daikuzono (10) Patent No.: US 6,302,878 B1
(45) Date of Patent: Oct. 16, 2001

(54) SYSTEM FOR LASER LIGHT IRRADIATION TO LIVING BODY

(75) Inventor: Norio Daikuzono, Cincinnati, OH (US)

(73) Assignee: S.L.T. Japan Co., Ltd., Tokyo (JP)

( * ) Notice: Subject to any disclaimer, the term of this patent is extended or adjusted under 35 U.S.C. 154(b) by 0 days.

(21) Appl. No.: 08/885,032

(22) Filed: Jun. 30, 1997

Related U.S. Application Data (63) Continuation of application No. 08/495,341, filed on Jun. 27, 1995, now abandoned.

(51) Int. Cl.$^7$ .................................................. A61F 7/00
(52) U.S. Cl. ............................... 606/7; 606/15; 606/16
(58) Field of Search ............................ 607/89; 606/3, 606/7–10, 13–17

(56) References Cited

U.S. PATENT DOCUMENTS

| | | | |
|---|---|---|---|
| 4,736,743 | | 4/1988 | Daikuzono . |
| 5,123,902 | * | 6/1992 | Müller et al. ........................ 606/15 |
| 5,209,748 | * | 5/1993 | Daikuzono ............................ 606/7 |
| 5,226,907 | * | 7/1993 | Tonkovich ............................ 606/9 |
| 5,242,438 | * | 9/1993 | Saadatmanesh et al. ............. 606/7 |
| 5,346,488 | * | 9/1994 | Prince et al. ........................ 606/15 |
| 5,409,483 | * | 4/1995 | Campbell et al. ................... 606/15 |
| 5,417,653 | * | 5/1995 | Sahota et al. ........................ 606/7 |
| 5,423,803 | * | 6/1995 | Tonkovich et al. .................. 606/9 |
| 5,423,805 | * | 6/1995 | Brucker et al. ...................... 606/7 |
| 5,431,648 | * | 7/1995 | Lev .................................... 607/101 |
| 5,445,608 | * | 8/1995 | Chen et al. .......................... 607/89 |
| 5,454,807 | * | 10/1995 | Lennox et al. ...................... 606/15 |
| 5,496,309 | * | 3/1996 | Saadat et al. ....................... 606/15 |

* cited by examiner

Primary Examiner—Robert L. Nasser
(74) Attorney, Agent, or Firm—McDermott, Will & Emery (57) ABSTRACT

The present invention relates to a system for irradiating a living body with laser light. The system is excellent in treatment effect by enhancing the absorption efficiency of laser light at a target area of the living tissue. The system comprises a target means located on the surface or in the inside of a living tissue to be treated including a material which absorbs the laser light to generate heat; and means for irradiating said target with the laser light to generate heat.

9 Claims, 8 Drawing Sheets

SYSTEM FOR LASER LIGHT IRRADIATION TO LIVING BODY

This application is a continuation of application Ser. No. 0/495,341 filed Jun. 27, 1995 abn.

DETAILED DESCRIPTION OF THE INVENTION

1. Field of the Invention

The present invention relates to a system for irradiating a living body with laser light, and in particular to a system for irradiating a living body with laser light which is excellent in therapeutic effect by enhancing the absorption effect of laser light at a target area in a living tissue,

2. Prior Art

Recently, incision, evaporation, solidification and hyperthermia treatment of a living tissue have been frequently conducted by irradiating the living tissue with laser light.

In this case, a non-contact irradiating method in which laser light is directly emitted toward a living body from an optical fiber positioned remotely from the living body is frequently conducted as well as a contact irradiating method in which laser light is emitted toward a living tissue from a light guiding probe provided in front of an optical fiber which is in contact with the living tissue as is disclosed, for example, in U.S. Pat. No. 4,736,743, filed by the present inventor.

Means having a layer containing heat absorbing powders which is formed in the tip end of a probe, for converting the energy of the laser light into thermal energy to facilitate the incision and/or solidification of the tissue is disclosed in the foregoing patent.

The contact method is advantageous in that positioning of the probe can be properly carried out with respect to a target position and in that the amount of laser light incident upon the tissue can be precisely controlled.

Although the distribution of the energy of the laser light emitted from a probe can be determined to some extent by selecting the configuration of the probe depending upon application, control in such manner that the laser light is incident upon a predetermined area, but is not incident upon the other area is impossible. Accordingly, unwanted area, other than target areas would be irradiated with the laser light. There is the risk that the tissue at the unwanted areas may be damaged.

If the diseased part to be treated is within the tissue, it is necessary to directly irradiate the diseased part, with the laser light after the tissue has been incised into the vicinity of the diseased part since the normal tissue from the surface to the diseased part would be otherwise damaged. This may be a cause of delay of the recovery or cure of the patient.

SUMMARY OF THE INVENTION

It is therefore an object of the present invention to reduce damage to the least possible amount of tissue other than the tissue to be treated by causing only the tissue to be treated.

It is another object of the present invention to reduce the damage to the sound tissue even if the diseased part within the tissue is irradiated with the laser light from the surface thereof.

In accordance with the present invention, there is provided a system for irradiating a living body with laser light, characterized in that it comprises a target means located on the surface or in the inside of a living tissue to be treated including a material which absorbs the laser light to thereby generate heat; and means for irradiating said target with the laser light to cause said heating generate heat.

Said laser light irradiating means preferably comprises a laser light emitting portion responsive to laser light from a laser light generator for emitting laser light; a cooling portion which is provided in at least a laser light emitting direction; and coolant supplying means for conducting coolant through said cooling portion.

The laser light irradiating means irradiates with laser light the target located on the surface or in the inside of a living tissue to be treated, including a material which absorbs the laser light to generate heat be heated thereby so that the material will generate heat while the cooling portion is in contact with the surface of the living tissue.

The laser light may be preferably pulsed laser light.

DESCRIPTION OF PREFERRED EMBODIMENT

In accordance with the present invention, a target is made by providing the surface of a living tissue, such as the skin surface or the inside of the tissue, such as the prostate, with a material which generates heat upon absorption of the laser light. The material which absorbs the laser light for generating heat (hereinafter referred to as "heat generating material") may include powders of inorganic material such as carbon powders, dyes, pigments, manganese dioxide, red oxide (Ferric oxide; ($Fe_2O_3$), iron oxide ($Fe_3O_4$), or powders of organic material.

This heat generating material may be applied to the target position as is. However it is preferable to disperse it in a medium such as water (preferably physiological salt water), alcohol and dextrose liquid, as well as heat resistant high molecular material. If necessary, it is possible to adjust the viscosity by adding to the dispersion liquid a binder, viscosity increasing agent, and the like. The heat generating material may be selected depending upon the type of the laser light used, particularly the wave length. Since Nd: YAG laser light tends to be absorbed by proteins, the protein material is implanted from an external position as the heat generating material.

Although the dispersion liquid may be applied on the surface of the living tissue, it may be injected into the tissue through a syringe needle piercing the tissue surface.

In the case of injection into the tissue, the heat generating material and dispersion liquid is selected in consideration of safety of the living body. In view of this, carbon, manganese oxide, iron oxide, or melamine is preferable as heat generating material.

Water and alcohol are preferable as the dispersion medium. A specific example of iron oxide is "Fesin" 9 available from Yoshitomi Seiyaku Co., Ltd.) which is vein-injected for treatment of iron deficiency anemia patients. This "Fesin" is referred to as sugar containing iron oxide (Ferric Oxide, $Fe(OH_3m\ F_{22}H_{22}O_{11}n)$).

Laser light irradiation of a target including the heat generating material of a position in interest causes the heat generating material to absorb the laser light for generating heat. As a result of this, degeneration of the tissue occurs so that the tissue is evaporated or solidified.

If no heat generating material exists, high energy laser light is necessary to cause the tissue in a position in interest to be evaporated or solidified. Therefore, damage may be caused at positions other than the treating position.

Figure 1:
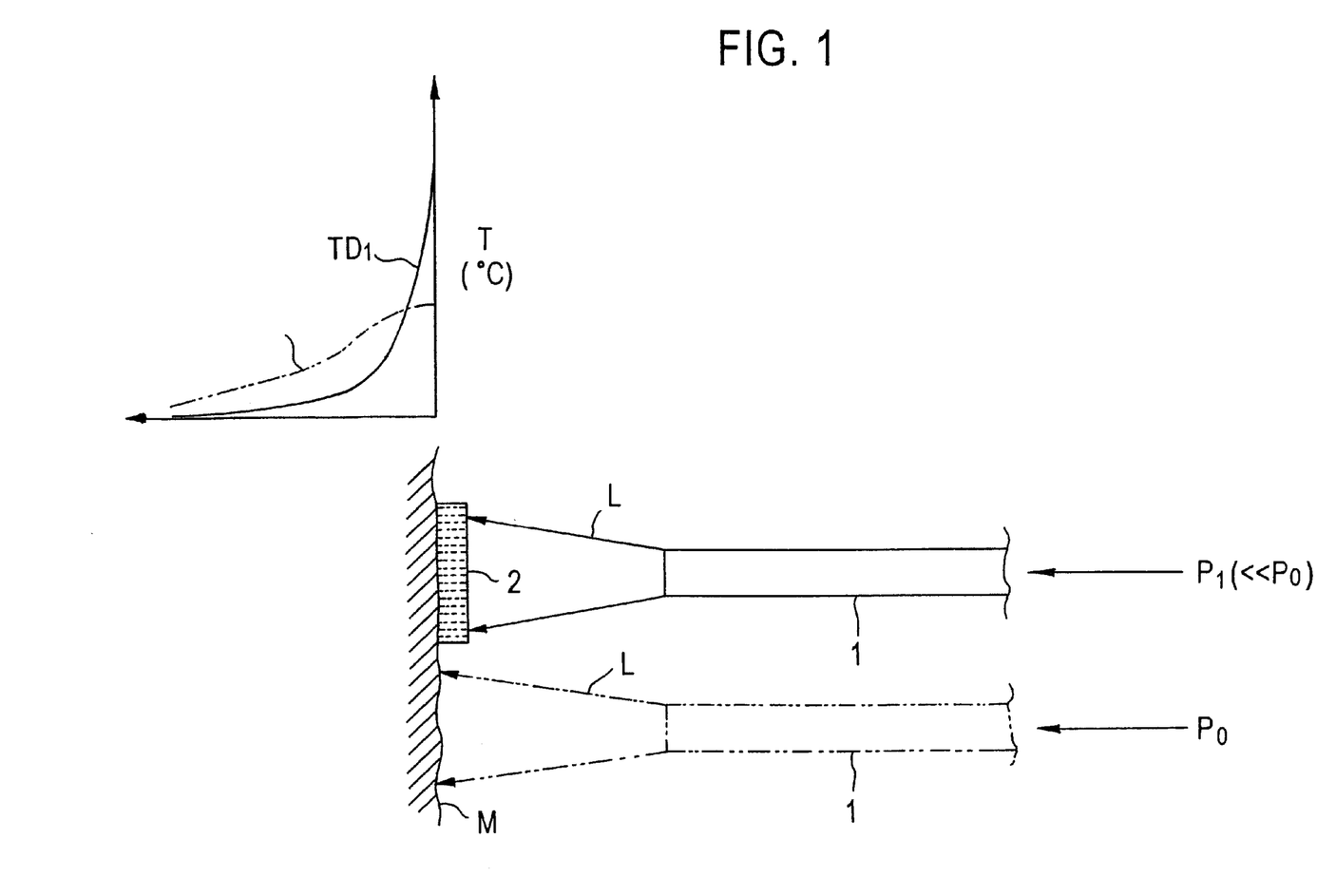
FIG. 1 is an explanatory view showing the manner of irradiation of the laser light in accordance with the present invention and the temperature distribution in a depth direction of the tissue.

This will be schematically explained with reference to FIG. 1, in which laser light L is incident upon the surface of the target tissue M from an optical fiber 1. When laser light having a power $P_0$ is incident upon the target position in which no heat generating material is present the temperature gradually decreases as shown by a curve representing the temperature distribution $TD_0$ in a depth direction of the tissue M, as represented by the two dotted curve. In contrast to this, if a layer 2 containing a heat generating material is preliminarily formed on the surface of the target tissue M, the temperature on the surface of the target tissue M is locally elevated since the heat generating material generates heat by being irradiated with laser light. Accordingly, a power P, of the laser light which is lower than $P_0$ is sufficient to obtain a desired-temperature on the surface of the target tissue. As is represented with the temperature distribution TD, in a depth direction of the tissue M, the temperature is abruptly lowered with the depth below the surface since the most of the laser light energy is consumed (absorbed) on the surface of the target tissue M. Consequently, in the treatment of a blotch on the skin and skin cancer, it is possible to cause only the blotch and cancer tissue to necrose and not damage any of the tissue below the blotch and the cancer tissue.

Figure 2:
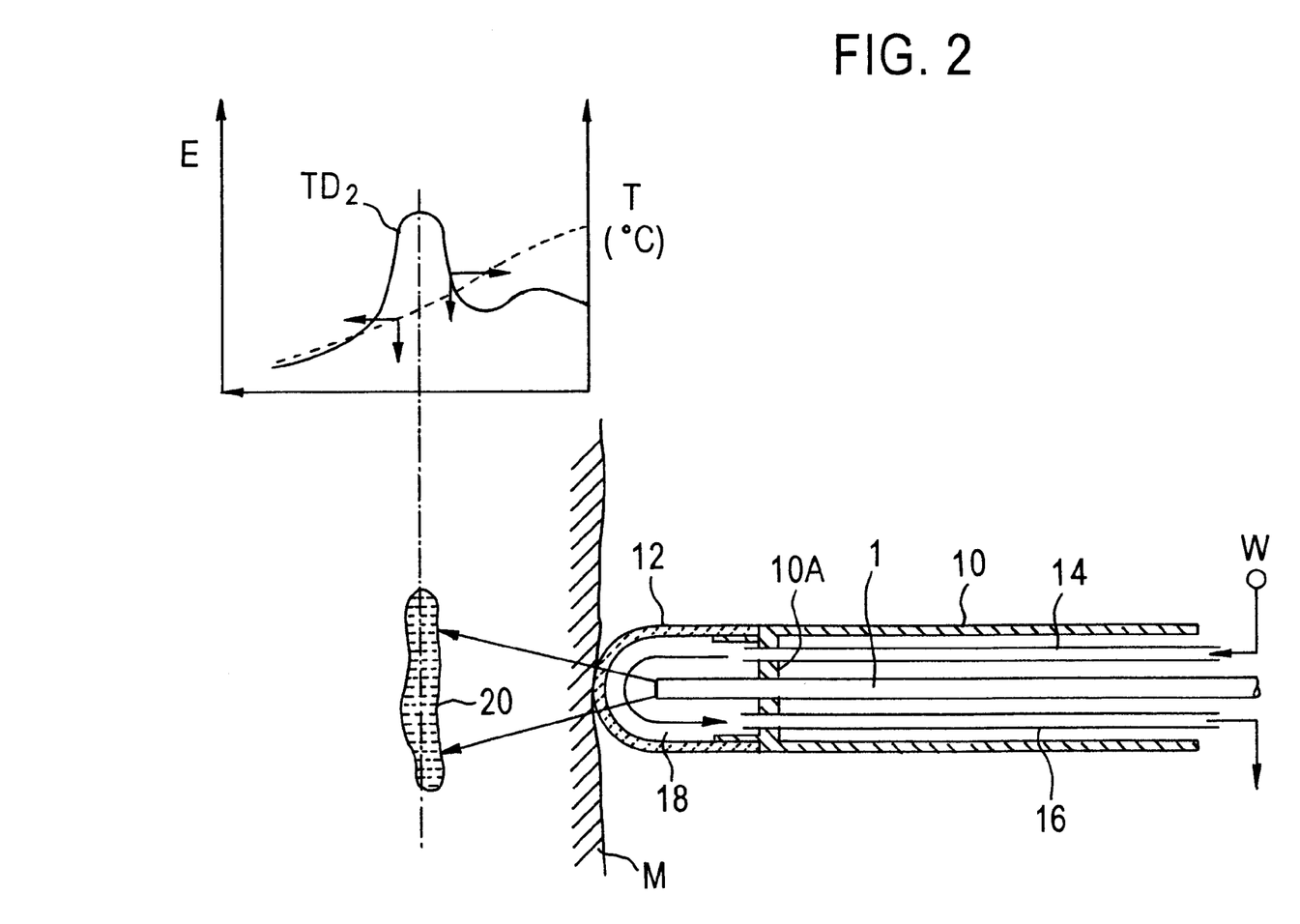
FIG. 2 is an explanatory view showing a method of cooling water circulating type of irradiation of the laser light in accordance with accordance with the present invention and the temperature distribution in a depth direction of the tissue.

As shown in FIG. 2, if the inside of the tissue is irradiated with the laser light, it is preferable to conduct the laser light irradiation while cooling the surface of the tissue. That is, a target zone 20 is preliminarily prepared by injecting a heat generating material containing dispersion liquid into the tissue M in a given position, for example, through a syringe needle.

A laser light irradiating device is used in which a cylindrical holder 10 is provided at the front end thereof with a guide window 12 made of a laser light transmittable ceramics or plastics. An optical fiber 1 is held at the center of the holder 10. Tubes 14 and 16 for supplying and discharging coolant, for example, water W are communicated with a communication chamber 18 defined by the guide window 12 and a partition wall 10A at the front end of the holder 10. The water W is supplied to the communication chamber 18 through the supplying tube 14 and is discharged through the discharging tube 18. The target zone 20 is irradiated with the laser light L from the laser light irradiating device while the water W is continuously or intermittently circulated.

In this case, the energy distribution E—of the laser light in a depth direction of the tissue M is such that it is gradually lowered from the surface of the tissue M, while the temperature distribution $TD_2$ is such that the surface area of the tissue M is forcedly cooled with water W flowing through the communication chamber 18 so that the temperature is lower than that if it is not cooled and the temperature corresponds to the incident energy in an area which is not cooled. The temperature is abruptly elevated due to heat generation in a deeper target zone 20. The temperature in the zone extending is also abruptly lowered below the target zone 20 since most of the energy of the laser light is consumed (absorbed) in the target zone 20.

Accordingly, in general terms, the target zone 20 is collectively heated so that evaporation and solidification of the tissue in this zone occurs. As is apparent from the temperature distribution TD, the temperature from the surface of the tissue to the target zone 20 is so low that the tissue in this zone is prevented from being damaged.

Figure 3:
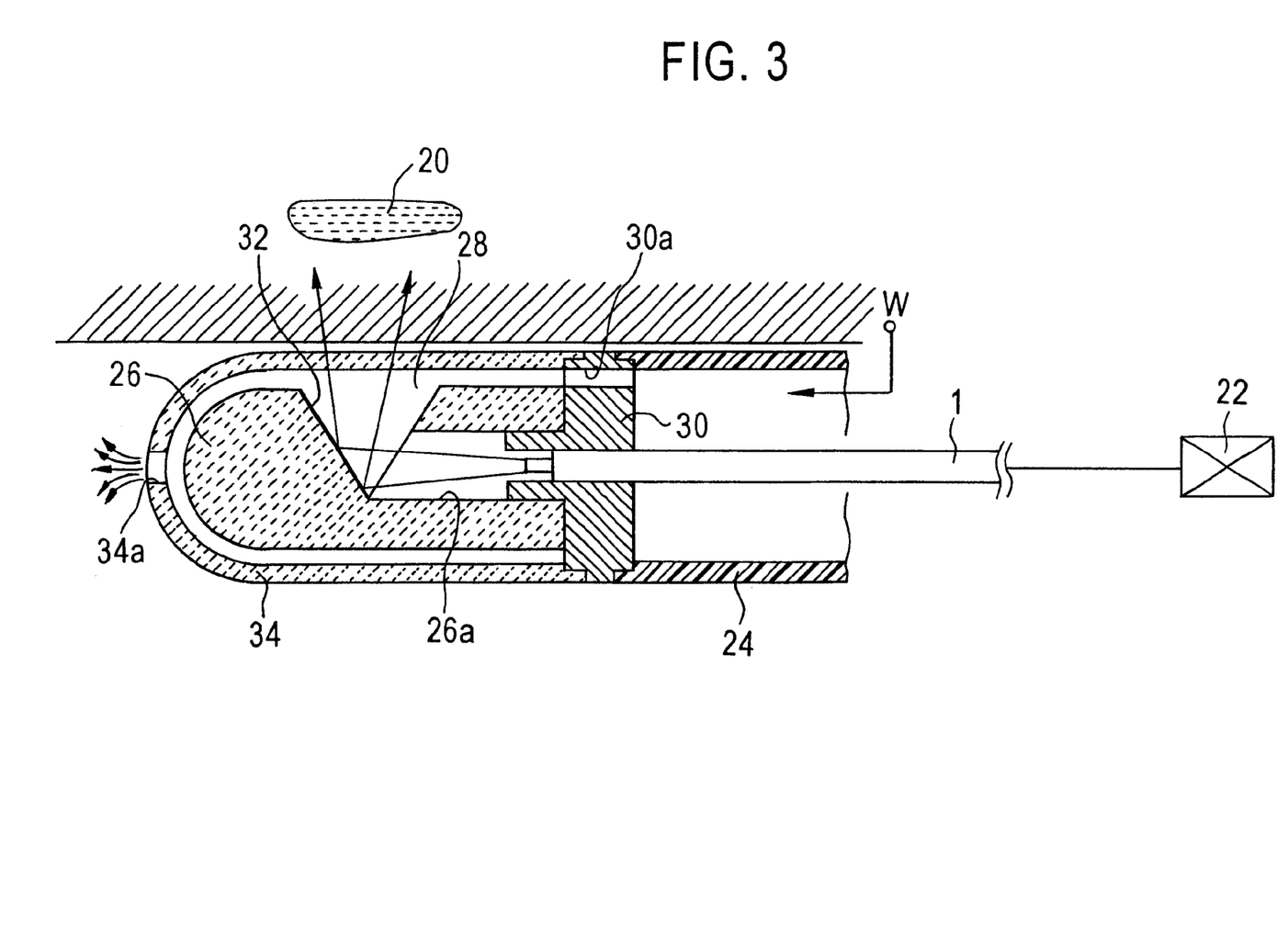
FIG. 3 is a longitudinal cross sectional view showing a system for irradiating laser light in a lateral direction.
Figure 4:
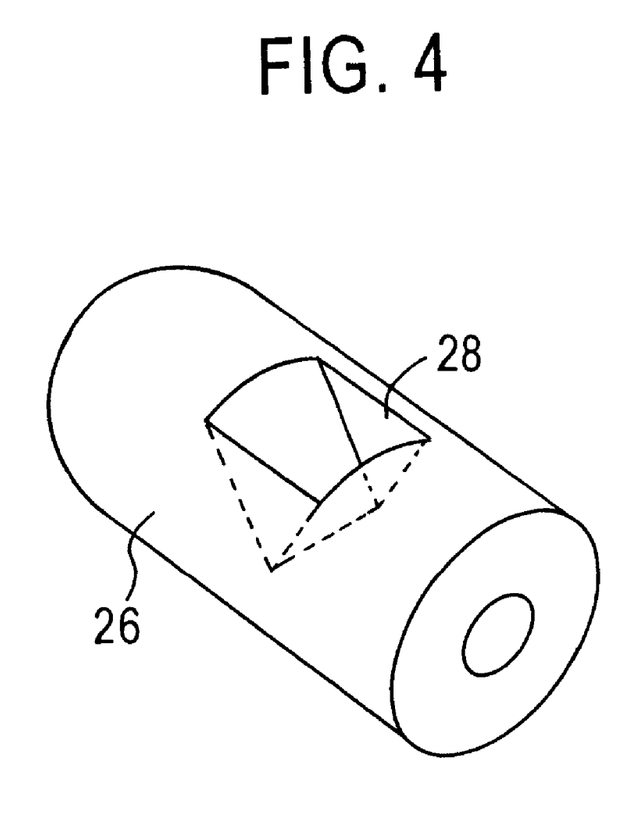
FIG. 4 is a perspective view showing a reflector for the system shown in FIG. 3.

A specific first example of cooling of the tissue surface in accordance with the present invention will be explained with reference to FIGS. 3 and 4. In this case, the front end portion of the irradiating device is inserted into a body cavity such as the esophagus, stomach, or large intestine. The target zone 20 which is located in the lateral direction with respect to the emission direction of the optical fiber 1, and comprises tissue such as cancer tissue is irradiated with the laser light for causing necrosis thereof.

The optical fiber 1 is optically coupled with a laser light generator 22. A protection tube 24 such as a plastic tube is provided so as to surround the optical fiber 1.

A reflector 26 is made of heat resistant ceramics or glass, artificial sapphire, and alumina. Stainless steel may also be used for the reflector 26. The reflector has an opening 28 on the side thereof. A through-hole 26a is formed so that it is in communication with the opening 28. A connector 30 is fixed to the end of the through-hole 26a for holding the front end of the optical fiber 1. The opening 28 of the reflector 26 is positioned at an angle of about 60 degrees in the longitudinal cross section. The reflector 26 is formed on the front side thereof with a gold plating layer 32.

On the other hand, a cover member 34 made of light transmitting glass is, for example, heat resistant glass connected with the protection tube 24 at the front end thereof through the metallic connector 30. The cover member 34 is formed at the front end thereof with an outlet 34a. Fluid, such as cooling water W is supplied to the space between the protection tube 24 and the optical fiber 1. The flange of the connector 30 is formed with one or more through-holes 30a.

Laser light is transmitted through the optical fiber 1 from the laser light generator 22 and is emitted from the front end of the optical fiber 1. The laser light is incident upon the gold plating layer 32 and is reflected thereon and is transmitted through the opening 28 and the cover member 34 and is impinged upon the target 20 within the tissue.

In the course of irradiation, the cooling water W is continuously supplied into the protection tube 24. The cooling water W flows through each of through-holes 30a of the connector 30 and then through the space between the reflector 26 and the cover member 34 and then exits from the outlet 34a. As a result, if the laser light irradiating device of the present invention is inserted in the body cavity, mucous will not enter into the inside of the cover member 34. On insertion into the stomach, gastric juice will not enter into the device. Accordingly, the inside of the cover member 34 is always kept clean.

On the other hand, since the inner space of the opening 28 and the through-hole 26a is always filled with cooling water W by the supplying thereof, a portion of the front end of the optical fiber 1 facing the through-hole 26a, and the reflecting surface, which is the gold plating layer 32 in the example, are cooled so that these portions will not be damaged by heat from the laser light even if the power of the laser light is high.

Figure 5:
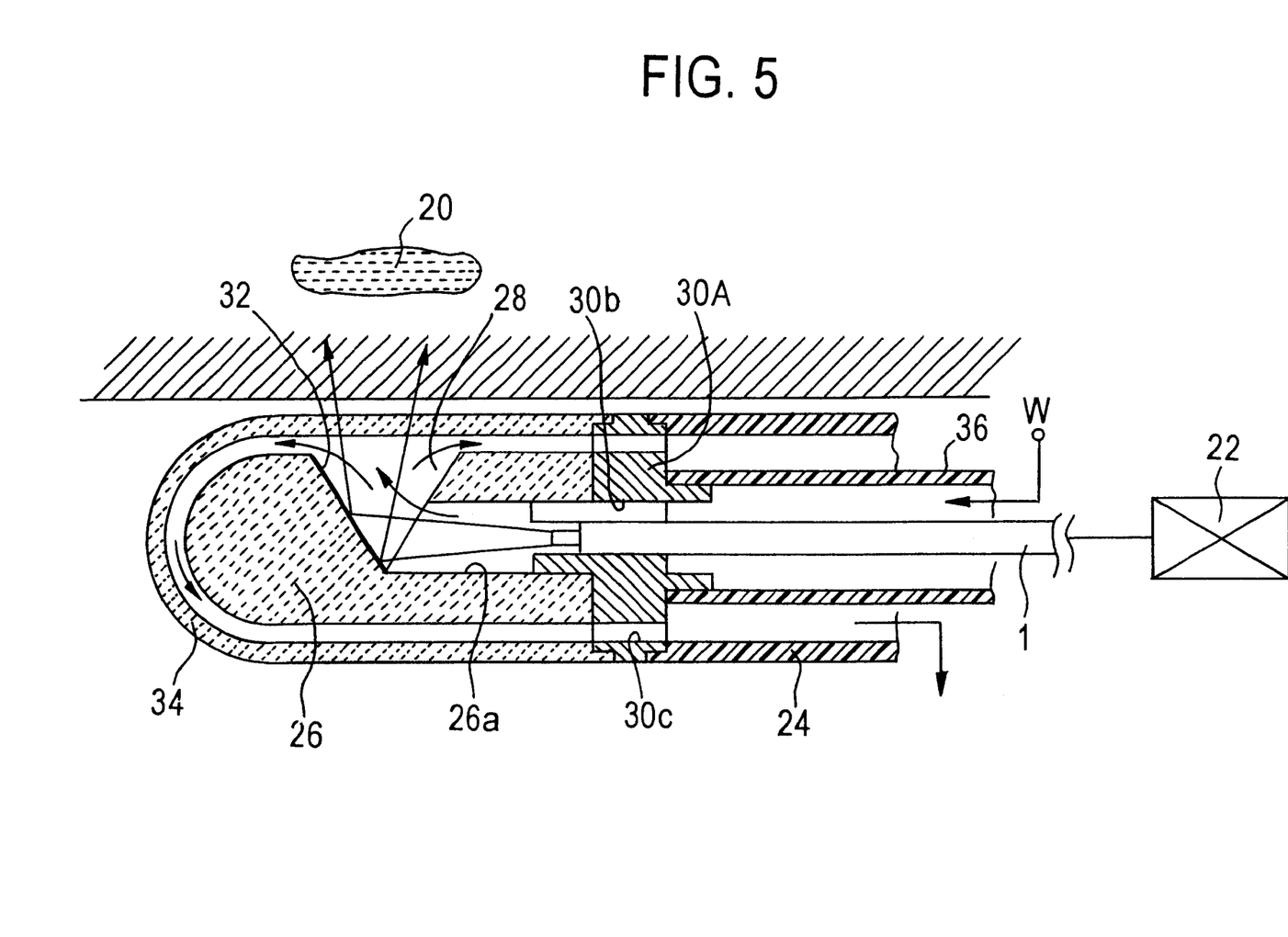
FIG. 5 is a longitudinal cross sectional view showing another system for irradiating laser light in a lateral direction.

FIG. 5 shows a second embodiment in which a protection tube 24 is connected by a cover member 34 by means of a sleeve-like connector 30c and a reflector 26 is connected with an optical fiber 1 by means of connector 30A which is formed with throughhole 30b, and a guide tube 36 is connected to the connector 30A so that it is communicated with the through-hole 30b.

In the second embodiment, cooling water W is also continuously supplied to the guide tube 36 in the course of laser light irradiation. The cooling water W flows through the through-hole 30b of the connector 30A to enter the through-hole 26a. The water then flows through the opening 28 and the space between the reflector 26 and the cover member 34. The water is then discharged externally of the device after flowing through the through-holes 30c of the connector 30A and a space between the guide tube 36 and the protection tube 24. Accordingly, the cooling water W flows one-way in the first embodiment while it is returned in the second embodiment.

Also in the second embodiment, the portion of the front end of the optical fiber 1 facing the through-hole 26a and the reflector 26 are prevented from being damaged since the cooling water W always flows through the through-hole 26a and the opening 28.

Figure 6:
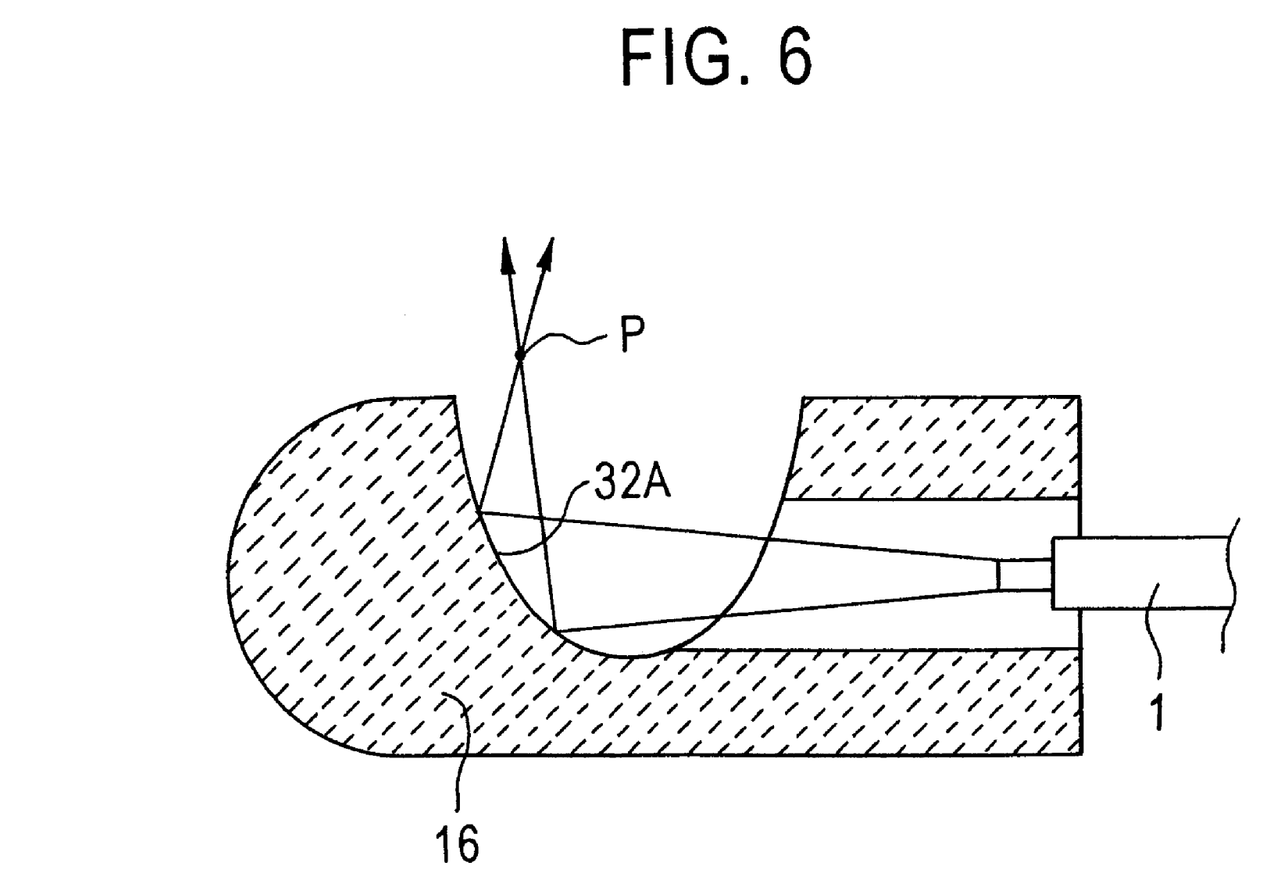
FIG. 6 is a perspective view showing another reflector for the system shown in FIG. 5.

FIG. 6 shows an example in which the reflecting face of the reflector 26 comprises a concave face 32A. Since the energy of the laser light is focussed on a point P by means of the concave face, effective heating of the target 20 can be achieved even if the power of the laser light is low.

A mirror having a thin thickness may be secured to the reflector with an adhesive agent. If the reflector is made of stainless steel, the reflecting surface may be formed by grinding the surface thereof.

Although the coolant is water in the former embodiment, it may be a gas such as air or nitrogen. The laser light may not be directly impinged upon the reflecting surface from the front end of the optical fiber and may be emitted from the front end of the optical fiber via a laser light transmitting medium in front of the optical fiber.

With such a coolant circulating coolant type device, invasion of body liquid or foreign material such as tissue fragments can be prevented and the light emitting front end of the optical fiber and the reflecting surface can be cooled so that they are protected from heat from the laser light.

A method of laser light irradiation while circulating the coolant in accordance with the present invention may be applied to, for example, the therapy of the prostate using a balloon catheter.

Figure 7:
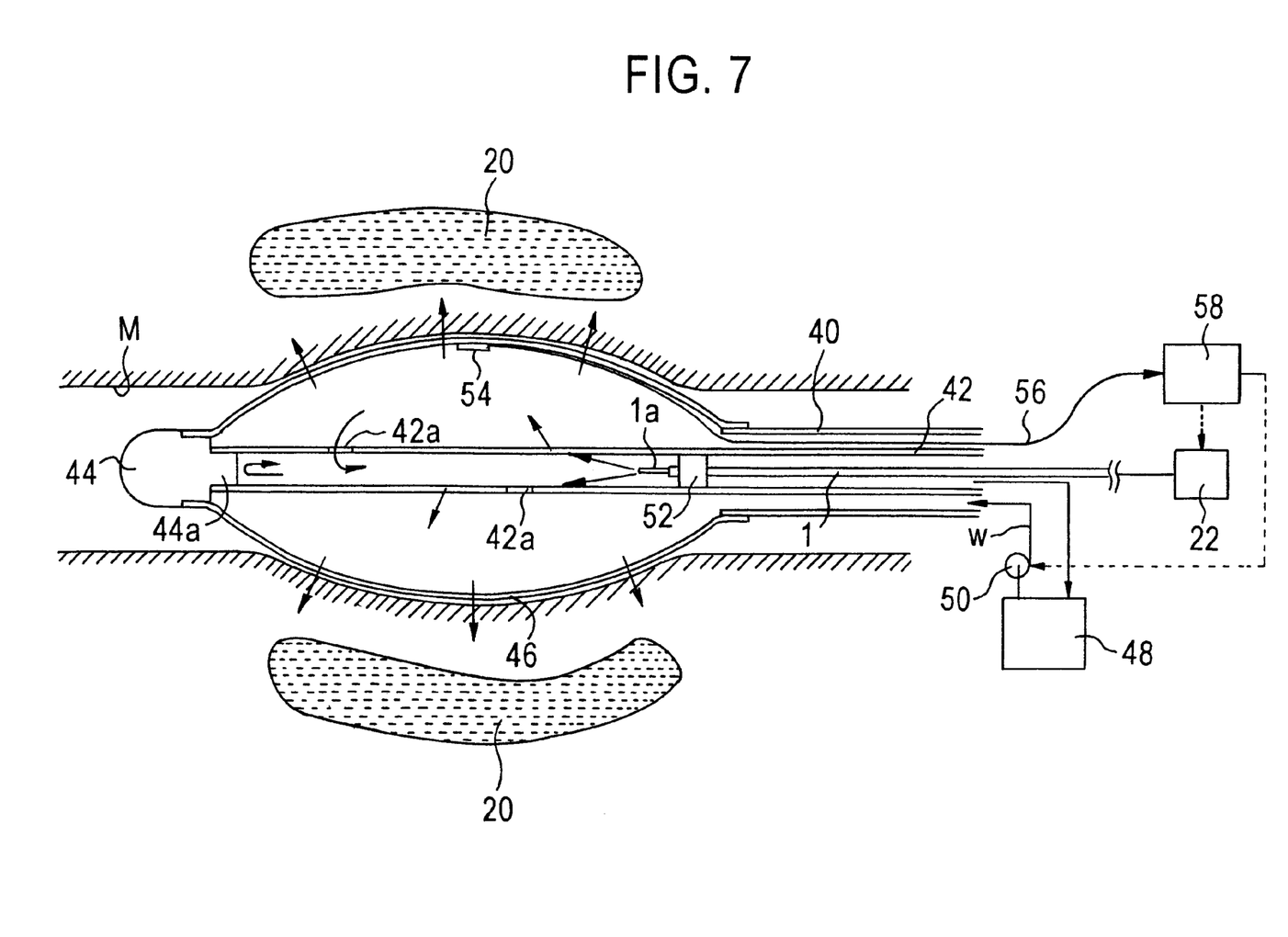
FIG. 7 is a schematic longitudinal sectional view showing a balloon catheter system.

FIG. 7 schematically shows a balloon catheter device in which a holding tube 42 made of, for example, a polyethylene tube, is coaxially disposed within an insertion tube 40 made of a polyethylene tube which is relatively flexible but is rigid to some extent and the holding tube 42 is provided with a metallic member 44 at the end thereof. A balloon 46 made of flexible rubber latex or plastics having ability to transmit the laser light is secured between the rear of the tip member 44 and the front of the insertion tube. The balloon 46 is inflated to bring it into close contact with the tissue M by differentiating between the amount of water supplied from the coolant reservoir 48 by a pump 50 and the amount of water returned to the coolant reservoir 48.

The optical fiber 1 is inserted into the holding tube 42 and is secured to the inner wall of the holding tube 42 via a holder 52. The holding tube 42 is made of a laser light transmittable material. Accordingly, the laser light is emitted around the holding tube 42 therefrom. Although some of the laser light is directed linearly forwards, it is reflected on the rear end face of a convex surface 44a of the tip member 44 since it has a reflecting ability provided by a gold plating thereon. Ultimately, the laser light is transmitted through the holding tube 42 and the wall of the balloon 46 and is directed toward the tissue M.

In order to diffusely emit the laser light from the front end of the optical fiber 1, it is preferable to expose a core portion at the front end portion of the optical fiber 1 as shown in the drawings, and/or to form a scattering layer having light scattering ability on the outer surface of the exposed portion 1a and/or to provide the outer surface with irregularities.

A thermocouple 54 is adhesively secured to the inner surface of the balloon 46. The conductors 56 lead externally of the device and are connected with a thermal controller 58.

In this laser light irradiating device, the balloon 46 is inflated by pumping the cooling water W by the pump 50 into the space between the insertion tube 40 and the holding tube 42 while the device is inserted into the tissue M. Some of the cooling water W enters into the balloon via the through-hole 42a of the holding tube 42 and is returned to the coolant reservoir 48 via a notch in the holder 52. This causes the vicinity of the inner wall of the tissue M to be cooled.

The laser light from the laser light generator 22 is emitted from the exposed core portion 1a at the front end of the optical fiber 1 while the cooling water is circulated in such a manner. The emitted laser light impinges the tissue M through the protection tube 42 and the balloon 46 to conduct the laser light irradiation therapy for a portion including the target 20.

The temperature on the surface of the tissue M is controlled by detecting it by means of the thermocouple 54, controlling the circulation amount of the coolant by means of the water pump 50, and/or by controlling the temperature of the coolant by means of a coolant temperature controller (not shown).

Figure 8:
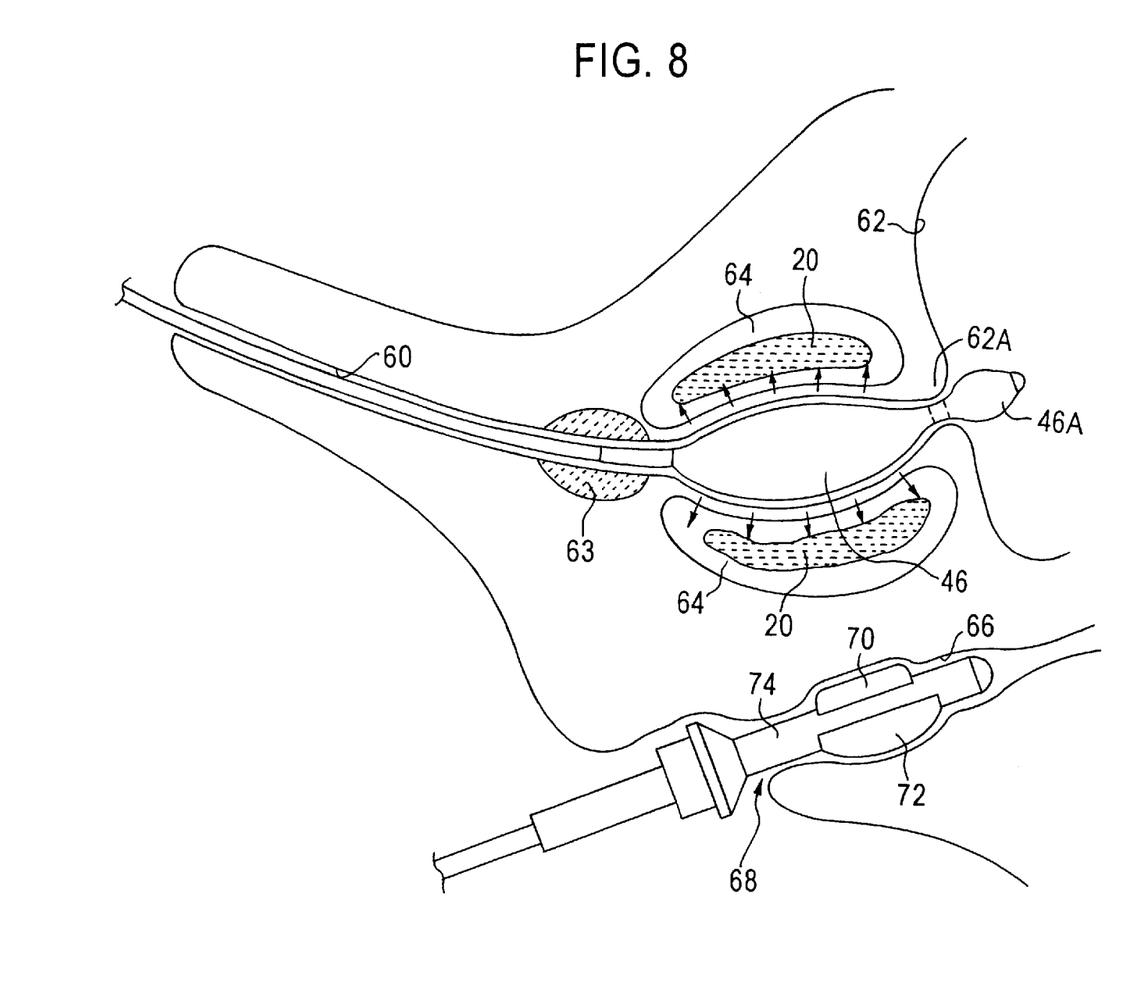
FIG. 8 is a sectional view showing an example of the prostate treatment to which the balloon catheter is applied.

FIG. 8 shows the manner in which the system of FIG. 7 is used for treatment of the prostate. A balloon catheter is inserted into the bladder 62 through the urethra 60. The illustrated balloon catheter is provided with a small balloon 46A at the front end of the balloon 46 to form a double balloon type. The small balloon 46A is inserted into the bladder 62 beyond a neck portion 46A thereof and is inflated during surgical operation so that it is hooked to the neck portion 62A to prevent the balloon catheter from being removed away from the urethra.

In this balloon catheter, the prostate 64 is irradiated with the laser light while the balloon 46 is inflated and cooling water is circulated through the balloon catheter.

When the prostate 64 is irradiated with the laser light, irradiation of only the inside of the prostate 64 as the target with the laser light and maintaining the inner wall of the urethra 60 at a low temperature achieves rapid curing after surgical operation. Therefore, irradiation with laser light while cooling the vicinity of the inner wall of the urethra and the sphincter portion 63 is effective.

Furthermore, prior to surgical operation a heat generating material is injected into the prostate by direct injection or vein injection. Since the target 20 into which material is injected is irradiated with the laser light, the target 20 is specifically heated so that the protein in the prostate is solidified to achieve post-operation curing.

Since excessive irradiation of the laser light may damage the prostate and the rectum 66, it is preferable to insert a rectum catheter 68 into the rectum 66 and "to control the energy of the emitted laser light by detecting the temperature of the inner wall of the rectum 66 by means of the thermal sensor 70. A biasing balloon 72 is inflated from the insertion portion 74 to bring the thermal sensor 70 into contact with the inner wall of the rectum 66 for enhancing the precision of the thermal control.

The present invention provides two modes, the former being irradiation of only the surface of the tissue with the laser light and the latter being irradiation of only the inside of the tissue.

It is preferable to provide pulsed laser light other than continuous laser light in both modes, particularly the former mode. Means for providing the laser light may be conventional.

What is claimed is:

1. A system for irradiating a living body with laser light, characterized in that it comprises:
   a target adapted to be located inside of a living tissue in a region to be treated, the target including a material which absorbs the laser light to thereby generate heat therefrom; and
   a means for irradiating said region to be treated from outside of said living tissue with the laser light to generate said heat in said target,
   said laser light irradiating means comprising:
      a holder having a laser light transmissive portion;
      a laser light emitting portion being provided within said holder and emitting laser light from a laser light generator to said laser light transmissive portion,
      a cooling portion being provided between said laser light transmissive portion and said laser light emitting portion;
      a closed-circuit cooling supply means for conducting coolant through said cooling portion;
      a temperature detecting means for detecting a temperature of the tissue in said region to be treated;
      a controller for controlling at least one of the circulation amount of the coolant supplied by the coolant supply means and the temperature of the coolant in response to the temperature of the tissue in said region to be treated as detected by said temperature detecting means; and
      wherein said laser light transmissive portion is adapted to be in direct contact with a surface of the living tissue so as to be spaced from and facing said region to be treated.

2. The system for irradiating a living body with laser light as defined in claim 1 in which the laser light is pulsated laser light.

3. A system for irradiating a living body with laser light, characterized in that it comprises:
   a target adapted to be located inside of a living tissue in a region to be treated, the target including a material which absorbs the laser light to thereby generate heat therefrom; and
   a means for irradiating said region to be treated from outside of said living tissue with the laser light to generate said heat in said target;
   said laser light irradiating means comprising:
      a holder having a laser light transmissive portion;
      a laser light emitting portion being provided within said holder and emitting laser light from a laser light generator to said laser light transmissive portion;
      a cooling portion being provided between said laser light transmissive portion and said laser light emitting portion;
      a coolant supplying means for conducting coolant through said cooling portion;
      wherein said laser light transmissive portion is adapted to be in direct contact with a surface of the living tissue so as to be spaced from and facing said region to be treated, wherein the target includes a sugar-containing iron oxide.

4. A method of irradiating a living body with laser light, which method comprises:
   inserting a target within a living tissue in a region to be treated, the target including a material which absorbs the laser light thereby to generate heat therein;
   positioning a laser light irradiating means comprising a laser light transmissive portion such that the laser light transmissive portion is in direct contact with a surface of the living tissue and spaced apart from and facing the region to be treated containing the target; and
   irradiating the region to be treated from outside of said living tissue with the laser light to thereby generate said heat in the target; wherein the laser light irradiating means further comprises:
      a holder having the laser light transmissive portion;
      a laser light emitting portion within said holder and emitting laser light from a laser light generator to said laser light transmissive portion;
      a cooling portion between said laser light transmissive portion and said laser light emitting portion;
      a closed-circuit coolant supplying means for conducting coolant through said cooling portion;
      a temperature detecting means for detecting a temperature of the tissue in said region to be treated; and
      a controller for controlling at least one of the circulation amount of the coolant supplied by the coolant supply means and the temperature of the coolant in response to the temperature of the tissue in said region to be treated as detected by said temperature detecting means.

5. The method according to claim 4, comprising pulsing the laser light.

6. The method according to claim 4, further comprising detecting a temperature of the tissue during laser irradiation.

7. A method of irradiating a living body with laser light, which method comprises:
   inserting a target within a living tissue in a region to be treated, the target including a material which absorbs the laser light thereby to generate heat therein;
   positioning a laser light irradiating means comprising a laser light transmissive portion such that the laser light transmissive portion is in direct contact with a surface of the living tissue and spaced apart from and facing the region to be treated containing the target; and
   irradiating the region to be treated from outside of said living tissue with the laser light to thereby generate said heat in the target; wherein the laser light irradiating means further comprises:
      a holder having the laser light transmissive portion;
      a laser light emitting portion within said holder and emitting laser light from a laser light generator to said laser light transmissive portion;

a cooling portion between said laser light transmissive portion and said laser light emitting portion;

a coolant supplying means for conducting coolant through said cooling portion; and wherein the target includes a sugar-containing iron oxide.

8. The method according to claim 4, wherein the target includes an inorganic or organic powder.

9. The system for irradiating a living body with laser light as defined in claim 1, wherein the target includes an inorganic or organic powder.

* * * * *